United States Patent [19]

Ko et al.

[11] Patent Number: 4,519,401
[45] Date of Patent: May 28, 1985

[54] PRESSURE TELEMETRY IMPLANT

[75] Inventors: Wen H. Ko, Cleveland, Ohio; Albert M. Leung, Kitchener, Canada

[73] Assignee: Case Western Reserve University, Cleveland Heights, Ohio

[21] Appl. No.: 534,094

[22] Filed: Sep. 20, 1983

[51] Int. Cl.$^3$ .............................................. A61B 5/00
[52] U.S. Cl. ..................................... 118/748; 73/721
[58] Field of Search ...................... 128/645, 748, 675; 604/118; 73/720, 721, 727

[56] References Cited

U.S. PATENT DOCUMENTS

| | | | |
|---|---|---|---|
| 3,853,117 | 12/1974 | Murr | 128/748 X |
| 4,080,653 | 3/1978 | Barnes et al. | 128/748 X |
| 4,281,667 | 8/1981 | Cosman | 128/748 |
| 4,407,296 | 10/1983 | Anderson | 128/478 X |

OTHER PUBLICATIONS

Macellari, "Batteryless Pressure Measurement", Med. & Biol. Eng. & Comput, 11/81, No. 6, pp. 686–694.
Ko, W. H., "Micro–Electronic Technology and Its Application to Bio–Telemetry", *Bio-Telemetry*, Pergamon Press, pp. 107–116, (1963).
Ko, W. H. and Slater, L. E., "Bio-Engineering: A New Discipline", *Electronics*, pp. 111–117, (Jun. 14, 1965).
Ko, W. H. and Neuman M. R., "Implant Biotelemetry and Microelectronics", *Science*, 156 (3773):351–360 (Apr. 21, 1967).
Lin, W. C., Ruffing, F. and Ko, W. H., "Feasibility Study of Electronic Multielectrodes Stimulation System for Visual Cortex Stimulation", Abstract from 23rd ACEMB—Washington Hilton Hotel, Washington, D.C. p. 166 (Nov. 15–19, 1970).
Ko, W. H. and Hynecek, J., "Dry Electrodes and Electrode Amplifiers", *Biomedical Electrode Technology*, Academic Press, N.Y., pp. 169–181 (1974).
Hynecek, J. and Ko, W. H., "Single Frequency RF Powered Telemetry System", Abstract from 28th ACEMB—Fairmont Hotel, New Orleans, Louisiana, p. 97 (Sep. 20–24, 1975).
Ko, W. H., Liang, S. P. and Fung, C. D., "Design of Radio–Frequency Powered Coils for Implant Instruments", *Medical and Biological Engineering and Computing*, 15:634–640 (Nov. 1977).
Ko, W. H., Bergmann, B. P. and Plonsey, R., "Data Acquisition System for Body Surface Potential Mapping", *Journal of Bioengineering*, 2:33–46 (1977).
Leung, A., Ko, W. H., Lorig, E., Cheng, D., Fleming, F. and Nulsen, J. Brodkey, "Intracranial Pressure Monitoring", Abstract from 31st ACEMB—Marriott Hotel, Atlanta, Georgia, p. 81 (Oct. 21–25, 1978).
Bettice, J. A., Leung, A., Lorig, R. J., Machtey, Y. and Ko, W. H., "Telemetric Intracranial Pressure Monitoring in Normal Goats", Abstract from 31st ACEMB—Marriott Hotel, Atlanta, Georgia, p. 324, (Oct. 21–25, 1978).
Ko, W. H., "Instrumentation for Neuromuscular Stimulation", *Functional Electrical Stimulation: Application in Neural Prosthesis*, Marcel Dekker, Inc., N.Y., pp. 515–526 (1978).
Plonsey, R., Ko, W. H., Liebman, J., Rudy, Y., Thomas, C. W. and Hunter, S., "ECG Body Surface Mapping Project at Case Western Reserve University", *Zbornik Radova Jurema*, 24:5 Svezak (1979).
Fleming, D., Bettice, J., Kocovsky, C., Zycer, I., Leung, A. and Ko, W. H., "A Totally Implantable Intra-Arterial Blood Pressure Monitor", Abstract from 32nd ACEMB—Denver Hilton Hotel, Denver, Colorado, p. 204 (Oct. 6–10, 1979).
Fleming, D., Bettice, J., Leung, A. and Ko, W. H., "An Implantable Telemetric Device for In Vivo Pressure Monitoring", Abstract from 1980 Joint Fall Meeting of American Physiological Society in Toronto, Canada (Oct. 12–17, 1980).
Sweeney, J. D., Leung, A. and Ko, W. H., "An Implantable Micropower Command Receiver for Telemetry Battery Power Switching", *Biotelemetry and Patient Monitoring*, 8(3):173–179 (1981).
Ko, W. H., Leung, A., Cheng, E. and Lorig, R., "Intracranial Pressure Telemetry System, I. Hardware Development", *Biotelemetry and Patient Monitoring*, 8(3):131–150 (1981).
Poon, C. W., Ko, W. H., Peckham, P. H., McNeal, D. R. and Su, N., "An Implantable RF–Powered Dual Channel Stimulator", *Biotelemetry and Patient Monitoring*, 8(3):180–188 (1981).
Ko, W. H., Bao, M–H and Hong, Y–D, "A High Sensitivity Integrated-Circuit Capacitive Pressure Transducer", *IEEE Transactions on Electron Devices,* ED-29(1):48–56 (1982).

Ko, W. H. and Fung, C. D., "VLSI and Intelligent Transducers", *Sensors and Actuators,* 2:239–250 (Jul. 1982).

*Primary Examiner*—Edward M. Coven
*Attorney, Agent, or Firm*—Watts, Hoffmann, Fisher & Heinke

[57] ABSTRACT

An implantable intracranial pressure (ICP) telemetry transmitter. Data transmission is accomplished by means of a radio frequency (RF) link coupled to a silicon piezoresistive pressure transducer. Electrostatic bonding of this transducer onto a tubular glass support provides long-term stability, stress isolation and a hermetic package. Because of the large temperature coefficient of the electrostatically bonded pressure transducer ($-6$ to $-9$ mm Hg/°C.), a temperature sensor is added to allow temperature compensation to be carried out. Pulse code modulation is employed to assure accurate data transmission. Use of low duty cycle pulse powering techniques lowers the power consumption of the telemeter. The complexity of the electronics is reduced by the use of a custom integrated circuit. Two lithium batteries can provide more than one month of continuous operation and an RF command receiver provides ON/Off control of the telemeter to extend the lifetime of the telemeter.

19 Claims, 15 Drawing Figures

PRESSURE TELEMETRY IMPLANT

DESCRIPTION

1. Field of the Invention

The invention relates to a surgically implantable device for measuring fluid pressure within a subject's skull or other body organs.

2. Background Art

In hydrocephalic children, a birth defect causes excessive cerebro-spinal fluid to be generated in the brain. Excessive fluid pressure constricts the flow in blood vessels of the brain resulting in brain damage. Additionally, the brain under such pressure does not develop normally. Both of these conditions lead to mental retardation and, eventually, to death.

A recently developed procedure to deal with this problem is to install what is known as a shunt. The shunt is a small conduit feeding from the brain area and "dumping" into the venous system, or into the stomach cavity. This relieves the pressure and sometimes prevents the tragic results. About 30% of the patients so treated will grow up to lead normal lives and sometimes the shunt can then be removed.

Other problems result, however, if a shunt drains excessive fluid from the intracranial cavity. This causes the intracranial pressure to drop to an excessively low level.

The brain is made up of various folds of tissue normally separated by pockets or cavities in between, called "ventricles". If insufficient fluid is present in the intracranial cavity, these ventricles will collapse. This also can result in brain damage and in severe headaches.

It is therefore apparent that it is highly desirable to maintain the intracranial pressure within a rather narrow range. If intracranial pressure can be monitored on a frequent basis, there are ways of adjusting the pressure. Sometimes, the shunt can be provided with a valve which can adjust the flow of fluid from the intracranial cavity. In other instances, medical treatment by the use of drugs has been effective in adjusting pressure.

Previously, pressure could be monitored only by an invasive technique. More specifically, a patch of the patient's hair is shaved off, and a needle is inserted through a small opening in the skull. A catheter attached to the needle delivers the fluid pressure to an external transducer which indicates intracranial pressure. The use of this invasive technique is limited in most patients to about once a month, and involves possible hazards of infection.

Several attempts have been made to devise implantable telemetry devices which can more conveniently, safely, and frequently be used to monitor intracranial pressure. One of these devices is described in an article entitled "Intracranial Pressure Telemetry System" by KO et al Biotelemetry Patient Monitg. 8:131–150 (1981). This article also describes some of the history of the development of such apparatus and is incorporated here by reference.

While the device disclosed in the article was successful in demonstrating that accurate monitoring is possible by way of an implantable device, there were several shortcomings, related to reliability, longevity, durability and cost.

The prior art device incorporated 60 integrated circuit chips. The multiplicity of these chips resulted in the need for numerous electrically conductive connections, which had to be made by hand. The number of these connections added greatly to the cost and complexity of the device, as well as degrading its reliablity.

A separate concern is device lifetime. Other devices in the past have used magnetic switches to turn the monitoring device on and off and thereby conserve power. These switches, however, are subject to inadvertent turn on when the patient is in the presence of magnetic fields no stronger than those often encountered in a home. Also, the magnetic switches are inconvenient since one needed to place the actuating magnet practically at the patient's skin. It was sometimes possible for a user to use the wrong end of the magnet, or to forget which way was on and which way was off.

Earlier devices were packaged in a capsule made from a metallic alloy including cobalt, nickel and iron. This alloy was used because its thermal coefficient expansion is almost the same as that of silicone. With such a capsule, temperature changes do not cause the capsule to pull away from the silicone used in the circuitry for monitoring the pressure. The mechanical relationships are very important, in view of the very small pressure differences which are desired to be detected.

This alloy, however, possesses several undesirable features. One relates to its propensity to corrode in body fluids. Salt is a corrosive material present in the body, and other body chemicals can also corrode metallic objects. Additionally the products of that corrosion can be toxic, even in small amounts.

When a capsule corrodes, a deformation of its walls can take place upsetting the desirable interface between the circuitry and the fluid whose pressure is being measured. Also, as edges become damaged, water molecules can enter the capsule resulting in changes in the calibration of the circuitry.

In the past, these alloy capsules have been gold plated to inhibit corrosion. This technique has been unsatisfactory since the gold tends to have pin holes and may separate from the alloy, and therefore does not always prevent corrosion. Also, there mechanical changes can affect adversely the interfacing between circuitry and pressure source.

DISCLOSURE OF INVENTION

The present invention provides a lightweight sturdy and long lasting implant for monitoring pressure variations in a subject. The unit is corrosive resistant and requires so little power that anticipated lifetime for the implant is years rather than months.

The implant includes a transducer for monitoring pressure variations and providing an electrical output related to those pressure variations. This transducer is mounted inside a telemetry unit which is coupled to a source of pressure, typically an intracranial cavity. The apparatus further includes a transmitter for converting the electrical output from the pressure transducer into a communications signal for transmission outside the implant. This transmitter includes a switch activated from outside the implant for causing the transmitter to switch from a quiescent state of low power consumption to a higher power transmitting state. The entire implant is hermetically encapsulated and therefore resists corrosion and degradation of the components with time.

The switching of the transmitter from a quiescent low power state to a higher transmitting state extends the lifetime of the transmitter. In accordance with a preferred embodiment of the invention, pulse code modulation is utilized so that even during the transmit mode of operation, an energy savings is realized. Thus, rather than continuously transmitting pressure signals from the intracranial region, the preferred embodiment of the invention periodically generates a pressure signal from the implant to a receiving unit where this pressure information is stored for subsequent monitoring.

In the quiescent state of operation, the circuitry draws only biasing currents from two small lithium batteries included in the implant. Upon receipt of the activation or ON signal from a remote transmitter, the implant switches states and power consumption rises to approximately 300 microwatts. The combination of low quiescent state plus pulse code modulation during transmission extends the life of the implant well beyond the lifetime expectancy of prior art monitoring implants.

The preferred packaging of the implant is a titanium package of commercial grade titanium rather than an alloy. The titanium is very corrosive resistant and is compatible with chemicals and/or fluids in the subject. The titanium package is also coated with a silicone rubber outside covering so that discomfort to the subject is minimized.

A preferred sensing transducer includes a piezo-resistive diaphragm which is electrostatically bonded on to a glass tube having a center portion communicating with the intracranial region of interest. This transducer is electronically coupled to a custom integrated circuit inside the titanium package and in combination with a CMOS analog-to-digital converter provides digital signals suitable for transmission.

A novel sterilization technique is utilized once the metal titanium package has been sealed. In accordance with this procedure, a hole is formed in the metal package to gain access to the various electronic components mounted therein. A sterilizing gas which in a preferred embodiment is ethyleneoxide is diffused through the hole into the region of the components. Once sterilization has been accomplished in this manner, the package is degassed by repeatedly applying vacuum and pressurizing the package. Finally the hole is sealed with a single pulse of coherent light from a laser.

It is known that the pressure recorded by an implant varies with temperature. For this reason, the circuitry includes a thermistor which is incorporated into a temperature sensitive pulse generating circuit coupled to the CMOS A-D converter. Changes in the pulse repetition rate of the pulse generator correspond to changes in the temperature of the fluid under scrutiny. The transmit rate of the transmitter also therefore becomes a function of temperature so that the monitoring system which records outputs from the implant simultaneously receives both temperature and pressure data.

In accordance with the preferred embodiment, a microcomputer based monitoring system is used to receive, store, and also analyze data from the implant. This microcomputer system automatically performs corrections due to temperature variation. The microcomputer system also includes an atmospheric pressure transducer so that corrections can be made with variations in atmospheric pressure. The data is corrected for these contributions and can be monitored on a video screen as well as stored within computer memory and output from a printer.

From the above it should be appreciated that one object of the invention is a compact, and accurate pressure monitoring implant. This and other objects and features of the invention will become better understood when a detailed description of a preferred embodiment of the invention is described in conjunction with the accompanying drawings.

BEST MODE FOR CARRYING OUT THE INVENTION

Figure 1:
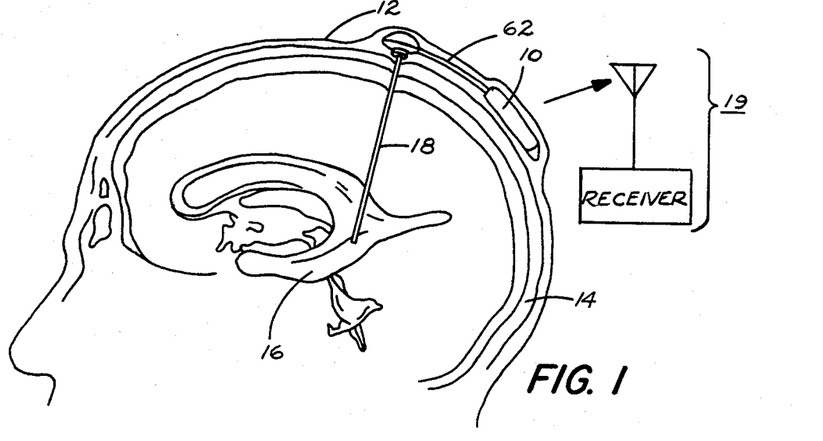
FIG. 1 is a schematic of a subject showing the positioning of an implant for monitoring pressure variations in an intracranial region of the subject.

Turning now to the drawings and in particular to FIG. 1, a telemeter 10 for monitoring pressure changes is shown implanted underneath a subject's scalp 12 on top of his or her skull 14. Pressure signals are measured from the lateral ventricle 16 through a fluid-filled catheter 18. Signals are conveyed to an external system through a radio frequency link 19.

Figure 2:
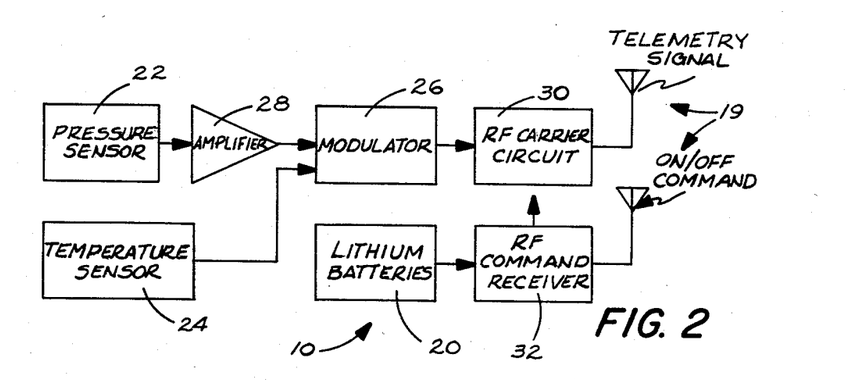
FIG. 2 is a schematic showing electronic circuitry needed to perform the pressure monitoring technique.

A simplified functional block diagram of the telemeter 10 is shown in FIG. 2. It is a totally implantable package powered by two miniature batteries 20. A signal from a pressure transducer or sensor 22 is processed and conveyed to an external system through the radio frequency link 19. A temperature sensor 24 is included so that temperature compensation of the pressure signal can be carried out at a receiver forming a part of that external system.

Sophisticated electronics are used to convey the pressure and temperature signal. A 10-bit pulse code modulator 26 receives an output from an amplifier 28 to provide accurate digital data signals for transmission by an RF carrier circuit 30. Comparable modulation schemes are not found in most biotelemetry because of the relatively high circuit complexity and power consumption. Making use of the high circuit density of custom monolithic integrated circuits, this high performance electronic system is implemented with only a few components.

Power consumption of the telemeter 10 is minimized by low duty cycle pulse powering. The overall power consumption of the complete circuit is only 0.3 mW. The two miniature lithium batteries 20, each measuring 12.5 mm in diameter and 2 mm in height, can provide up to one month of continuous operation. A CMOS RF command receiver 32 provides ON/OFF control of the telemeter 10. Based on a two hour per day usage, the battery lifetime can be extended to more than a year. With this telemeter 10, the capacity of the power source is less critical and even smaller batteries can be used.

A piezoresistive pressure sensor 40 (FIG. 3) is used as a small size, and simple interface to the telemetry electronics. The Four p-type resistors, connected in a bridge configuration, are diffused onto one side of a 7 mil thick double polished N(100) silicon substrate 42 (resistivity 1 to 4 cm). A cavity 44 underneath the resistor bridge is obtained by anisotropic silicon etch producing an 0.8 mil silicon diaphragm 46. When differential pressure is applied, the diaphragmatic stress produces a differential bridge output proportional to the pressure. This pressure output is coupled to the amplifier 28 via four diffused conductors 50 leading to corresponding contact pads 52.

Figure 4:
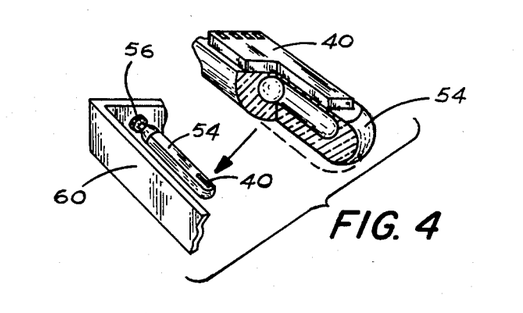
FIG. 4 is a perspective exploded view showing the pressure transducer mounted in a glass tube.

This pressure sensor 40 is electrostatically bonded onto the polished side of a Corning code #7740 glass tube 54 (3 mm OD, 0.6 mm wall) as shown in FIG. 4. A 15 mil diameter hole 55 underneath the pressure sensing diaphragm provides pressure signal communication between the inside of the glass tube 54 and the pressure sensing diaphragm 46.

Figure 5:
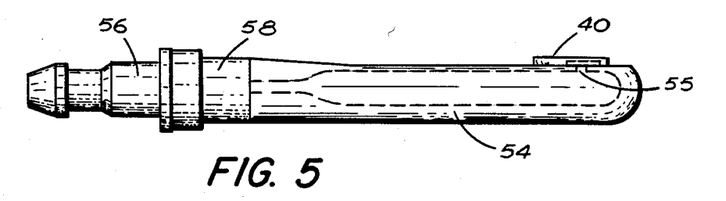
FIG. 5 is an elevational view of the transducer mounting.
Figure 6:
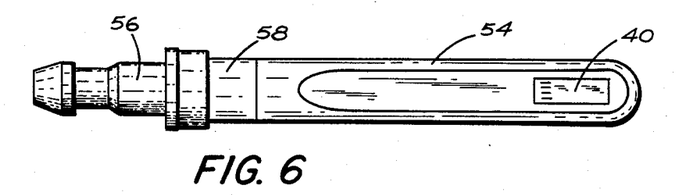
FIG. 6 is a plan view of the mounting.
Figure 7:
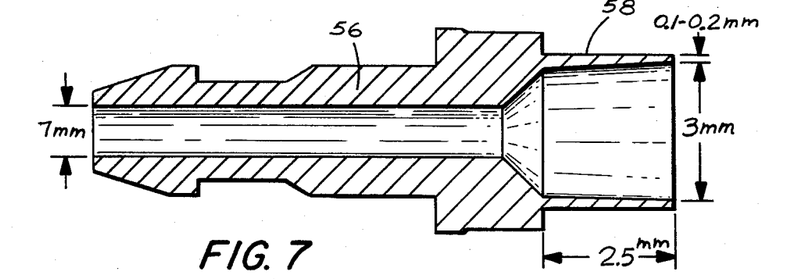
FIG. 7 is a sectioned view of a titanium adaptor for coupling to the glass mounting tube.

An opposite end of the glass tube 54 is thermally sealed to a titanium adaptor 56 (FIGS. 5-7). A 7 mil flange 58 of the adaptor 56 is then welded onto the side wall of a 0.8×1.2×0.25 inch titanium flat pack 60 which houses the telemetry electronics (see FIG. 8).

Figure 8:
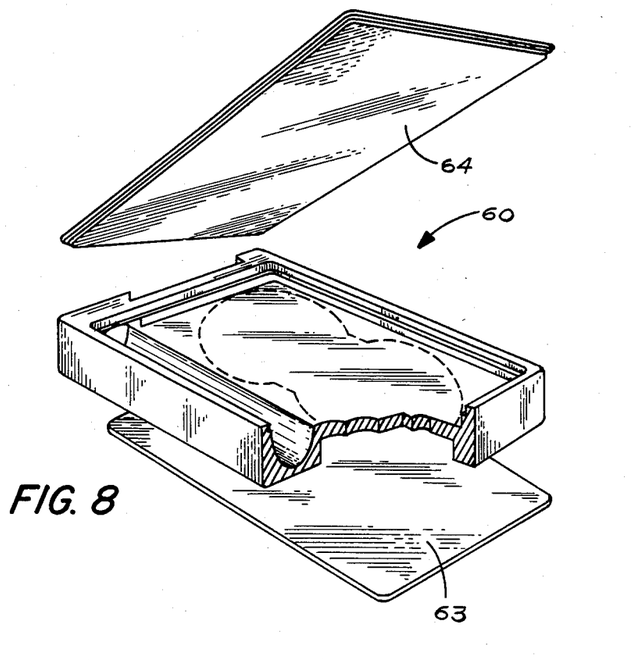
FIG. 8 is a perspective exploded view showing a titanium flat pack into which the circuitry schematically illustrated in FIG. 2 is mounted.

The end of the titanium adaptor 56 which is outside the flat pack 60 is connected to the pressure source through a fluid-filled silicone rubber tube 62. Through the center opening of the adaptor, the inside of the composite glass tube and the 15 mil hole, the pressure signal is thereby coupled from the source to the cavity side of the silicon pressure sensing diaphragm 46.

After all the electronics are assembled, the package 60 is sealed by laser welding a bottom 63 and top 64 covers onto it. Since the silicon-to-glass, glass-to-glass and glass-to-metal seals of the pressure transducer packaging are all made hermetic, the inside of the flat pack 60 is used as an hermetically sealed pressure reference chamber. This packaging technique is designed to protect the electronics and pressure transducer inside the flat pack and provide an absolute barrier against invading moisture.

The piezoresistive elements are located on the diaphragm's surface, well protected inside the flat pack so that instability caused by moisture-induced shunting current across its input/output leads is eliminated. Although the other side of the silicon diaphragm is exposed to the pressure carrying fluid, it has no effect on the electrical properties of the pressure sensing diaphragm because of the absence of any electric field or exposed circuit element.

The glass tube 54, onto which the pressure sensing diaphragm is bonded, is supported only on the adaptor end. The large length to diameter ratio of the glass tube effectively isolates the presssure sensing diaphragm 46 from any stress which might be transmitted from the titanium package.

A titanium adaptor 56 machined to precise tolerance is used to connect the glass tube 54. The thin wall 58 (FIG. 7) of the adaptor is important for stress reduction, because the thermal expansion coefficients of glass and titanium differ significantly. The thin wall section of the adaptor is sealed to the outside wall of the glass tube 54. In this manner the radial stress developed on the glass tube will be compression. Since the strength of the glass in compression is much larger than its tensile strength, this configuration gives a satisfactory seal. The glass tube titanium seal is carried out in an argon environment to preserve the ductility of titanium. The titanium adaptor itself is used as a susceptor in an induction furnace. In this manner only the glass in contact with the titanium will be heated to the working temperature.

Prior to electrostatic bonding both the silicon pressure sensing diaphragm 46 and the polished Pyrex glass tube 54 require ultrasonic cleaning in trichloroethylene, acetone and methonal. After blowing dry, the silicon pressure sensing diaphragm is assembled on top of the Pyrex glass tube. The 15 to 20 mil hole in the glass tube is centered underneath the silicon diaphragm. A 20 mil thick silicon block is then placed on top of the silicon pressure sensing diaphragm in order to protect it from mechanical damage. A carbon electrode is then placed vertically on top of the silicon block. By adding an 800 to 1000 gm weight to the top of the carbon electrode, a pressure is produced between the sealing surfaces. This setup is then heated to 340 ±10C. on a hot plate in a nitrogen environment. When this temperature is reached, a positive voltage, which is gradually increased from 0 to 1000 V in about five seconds, is applied to the carbon electrode with respect to the glass. The current is monitored by an analog meter and a chart recorder. An initiative sealing current reaches about 100 u A which quickly decreases to about 10 u A in a few minutes. After the voltage has been applied for about five minutes, the hot plate is turned off. As the temperature drops, the current decreases rapidly from 10 u A to a negligible amount. The dc voltage is turned off when the temperature has reached 150° C. and the sealing procedure is completed.

This sealing process, however, produces large leakage currents across the isolation junctions of the diffused resistor elements. This is due to the large field involved at high temperatures which drives most of the $Na^+$ ions in the silicon dioxide layer towards the silicon-silicon dioxide surface. By annealing the device at 300° C. for a few hours, this undesirable effect is eliminated.

Commercially pure titanium (greater than 99%) is utilized for the package 60 and adapter 56. The pure titanium package is coated with a layer of silicone rubber which pads the electronics inside the package as well as making the implant more comfortable for the subject.

Sterilization for human implantation is accomplished by drilling a hole on the top cover 64 and diffusing ethylene oxide gas into the package 60. After all the components have been sterilized the package 60 is degassed by alternate application of vacuum and pressure and then resealed with a single pulse from a laser.

The sensitivity of the transducer is 10 to 20 uV/mm Hg-V and has a linearity better than ±0.2% FS. Overpressure of more than 2000 mm Hg can be tolerated by the transducer. The device also demonstrates sufficient stability after an aging period. However, the temperature coefficient is fairly high (−6 to −9 mm Hg/°C.)

and temperature compensation must be employed to allow accurate pressure measurement.

Figure 9:
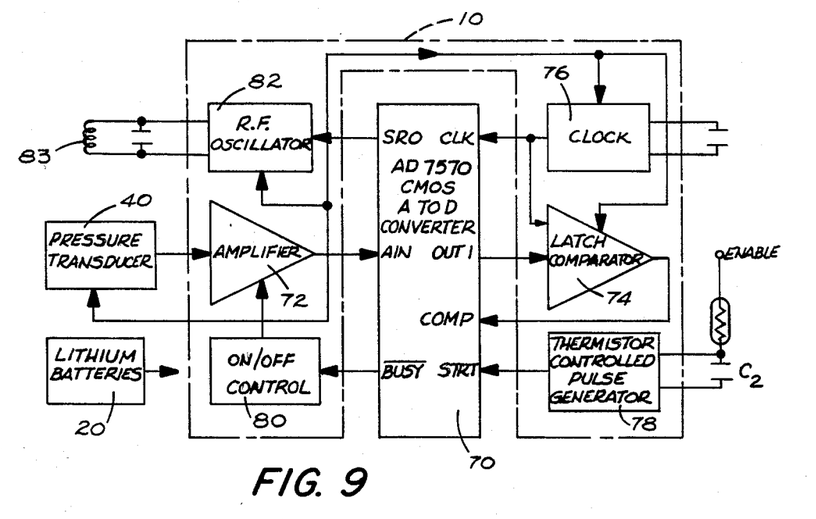
FIG. 9 is a more detailed schematic showing various components of a telemeter for monitoring and transmitting pressure data from the subject.

A block diagram of the transmitter portion of the telemeter 10 is shown in FIG. 9. An AD7570 CMOS successive approximation A/D converter 70 is incorporated for its high speed, low power consumption and potential for low duty cycle pulse powering applications. A pressure transducer amplifier 72, latch comparator 74, clock circuit 76, temperature controlled pulse generator 78, ON/OFF controller 80 and an RF carrier circuit 82 are provided by a custom bipolar integrated circuit.

In order to minimize power consumption, a pulse powering scheme is employed. When the pressure signal is sampled, the aperture time of the sampler is usually only a small fraction of the sampling period. If the pressure transducer is powered only during this aperture time, the average power consumption can be reduced by two to three orders of magnitude.

The power consumption of the RF carrier circuit 82 can also be greatly reduced by pulse powering. When low duty cycle pulses are used, the average power consumption can be reduced significantly. The circuit 82 is coupled to an RF coil 83 which is outside the titanium package 60 but encapsulated in epoxy. Leads to the coil 83 pass through holes in the package 60 have gold plating where the leads feed through the holes.

Similar techniques are applied to other circuit components in order to minimize the overall power consumption. The command receiver 80, however, is powered continuously because of its negligible quiescent power consumption. Certain details of each of these circuits will be described by reference to FIG. 10.

Thermistor Controlled Pulse Generator

The Thermistor Controlled Pulse Generator 78 is used as a pulse frequency modulator. It produces narrow pulses with pulse widths between 10 to 20 us. At 37.8° C. the nominal pulse frequency ($1/T_\theta$) is 100 Hz. This frequency is modulated by a thermistor 84 to produce a change of 5%/°C. Each pulse at the input labeled STRT on the A to D converter 70 initiates the acquisition, processing and transmission of one pressure signal sample from the sensor 40. Thus, the sampling frequency of the pressure readings is modulated by temperature.

Since the battery supply voltage is not regulated, the frequency of this circuit 78 is designed to have insignificant dependence on the supply voltage. Low power consumption is also essential. The disclosed circuit meets both the frequency stability ($-0.9\%/V$ at $V_{CC}=5.6$ V) and low power consumption (approx. 10 uW) requirements.

A Fenwal Model GA 72J2 (Fenwal Electronics, Framingham, Mass. 01701) thermistor is chosen as the temperature sensor 84. It is a high resistance, glass bead thermistor which has the advantage of low power consumption and good long-term stability. The norminal resistance of the thermistor is 10 Mohm at 37.8° C. and has a temperature coefficient of $-5\%°C$.

Figure 10:
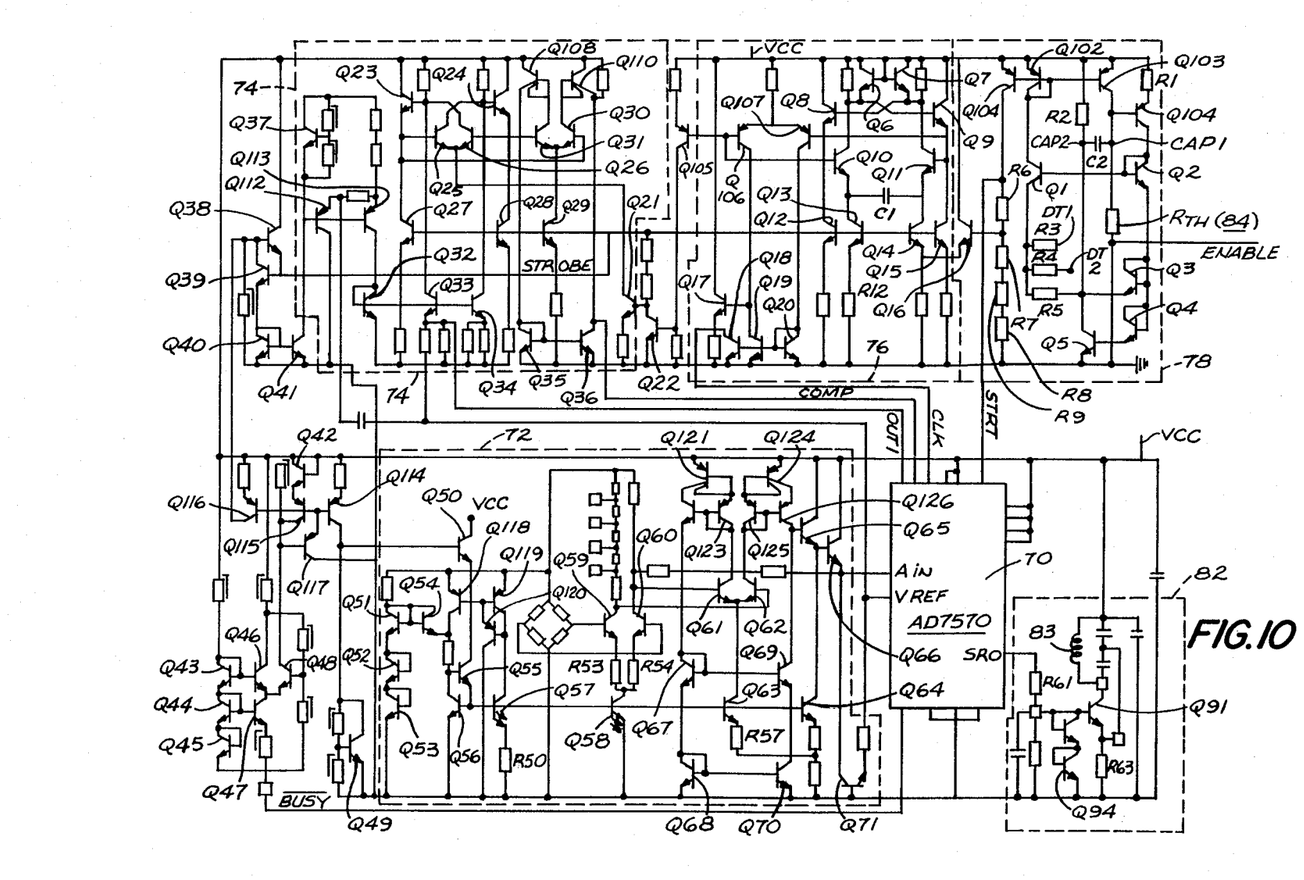
FIG. 10 is a detailed schematic of the telemeter of FIG. 9.

The Thermistor, $R_{TH}$, as shown in FIG. 10 is used to discharge a capacitor, $C_2$, when the circuit is in the discharge mode. Before the voltage at node CAP1 falls below a value of $(V_{CC}-V_{BE})$ where $V_{BE}$ is the base emitter ON voltage of a transistor $Q_{104}$, all transistors in the circuit 78 are operating at their cutoff region and the complete circuit consumes no current other than the discharging current through the thermistor $R_{TH}$. The base-emitter ON voltage of both the PNP and the NPN transistors is taken as $V_{BE}$ in the following analysis.

When the voltage at Node CAP1 falls to $(V_{CC}-V_{BE})$, $Q_{104}$ starts to conduct. Because of the positive feedback produced by $Q_5$ and $C_2$, all transistors in this circuit reach full conduction instantaneously. This puts the circuit into a charging mode. The negative feedback through $Q_3$ maintains the collector voltage of $Q_5$ at $V_{BE}$. Since the base of $Q_1$ is biased at $3 \times V_{BE}$ by the series connection of the base emitter junctions of $Q_2$, $Q_4$ and $Q_5$, the collector current of this transistor is equal to $V_{BE}/R_5$. This current is mirrored by $Q_{103}$ and $Q_{101}$ to charge $C_2$ and, at the same time, produce a logic 1 at the output labeled STRT.

When the voltage at node CAP1 reaches $(V_{CC}-V_{BE})$, the collector current of $Q_{104}$ diminishes producing a rise in the collector voltage of $Q_5$. This voltage change is coupled to the base of $Q_{104}$ further cutting off $Q_{104}$ and other transistors. This will put the whole circuit back into the discharge mode. The output pulse width, $T_{ST}$ at node STRT is equal to the charging time given by the following equation.

$$T_{ST} = R_5 C_2 (V_{CC} - V_{BE})/V_{BE} \quad (1)$$

By connecting nodes DT1 and/or DT2 to node CAP2, the charging current can be increased to shorten $T_{ST}$.

When the circuit changes from the charge mode into the discharge mode, the voltage at node CAP2 is switched from $V_{BE}$ to $V_{CC}$ (assuming negligible voltage drop across $R_2$ due to the capacitor charging current). The same voltage increase, $(V_{CC}-V_{BE})$, is produced at node CAP 1, raising the voltage at this point from $(V_{CC}-V_{BE})$ to $(V_{CC}-V_{BE}) \times 2$. This voltage then discharges towards the ground potential (0 V) through $R_{TH}$. As the voltage at node CAP1 reaches $(V_{CC}-V_{BE})$, switchng occurs and the cycle repeats itself.

The pulse period, $T_\theta$, is equal to the time required for the voltage at CAP1 to decay from $2 \times (V_{CC}-V_{BE})$ to $(V_{CC}-V_{BE})$ and is given by $$T_\theta = R_{TH} C_2 \ln 2 \quad (2)$$

It should be pointed out that the transistor $Q_1$ serves an important function in the proper operation of this circuit. As the voltage at node CAP1 goes above $V_{CC}$, the base-collector junction of $Q_{103}$ is forward biased. By connecting $R_5$ directly to the base and collector of $Q_{102}$, the capacitor, $C_2$, will be discharged towards $V_{CC}$ through $R_5$ and $R_2$. The resulting period, $T_\theta$ will be decreased.

The output current at the collector of $Q_{101}$ produces a voltage pulse across the pinch resistors $R_6$, $R_7$, $R_8$ and $R_9$. The parasitic diode in parallel to $R_7$, $R_8$ and $R_9$ limits the output voltage at node SYNC to $3 V_{BE}$ which is used to synchronize the clock circuit 76.

Clock and Comparator

Figure 11:
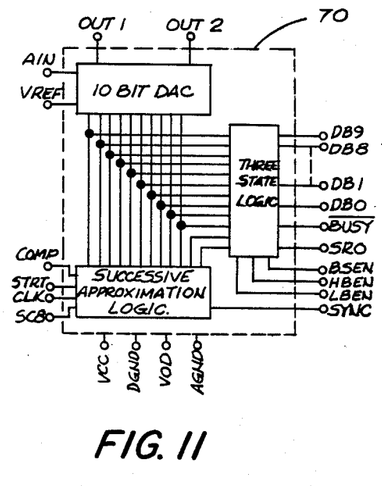
FIG. 11 is a schematic showing the construction of a CMOS analog-to-digital converter used in producing the invention.

A functional block diagram of the AD7570 circuit 70 is shown in FIG. 11. It requires an external clock circuit and a comparator for proper operation. The AS7570 has an internal clock which can operate with the addition of one external resistor and one capacitor. The frequency of this internal clock is a strong function of supply voltage. When two lithium batteries are used and the power supply voltage is not regulated, the supply voltage can drop from 6.0 V at the beginning to 5.2 V voltage near the end of the batteries' lifetime. This can decrease the clock frequency by as much as 30% which causes misinterpretation of as many as six data bits. In order to ensure correct data interpretation, a more stable external clock 76 must be used.

The external clock circuit 76 consumes negligible amounts of power (less that one microwatt) when it is inactivated through current switching. This permits significant power reduction by low duty cycle pulse operation.

A simple emitter-coupled oscillator configuration is chosen for its simplicity and high speed. As shown in FIG. 10, this oscillator consists of a capacitor $C_1$, and transistors $Q_6$–$Q_{15}$. The analysis of this circuit can be found in many circuit design textbooks and is not repeated here. The frequency of oscillation is found to be $$f = \frac{I}{4 C_1 V_{BE}} \quad (3)$$

Since the base voltage of $Q_{12}$–$Q_{15}$ is 2 $V_{BE}$ when the circuit is in operation, the current, I, is found to be $$I = \frac{V_{BE}}{R_{12}} \quad (4)$$

Substituting equation 4 into equation 3, the frequency becomes $$f = \frac{1}{4 R_{12} C_1} \quad (5)$$

or $$T = 4 R_{12} C_1 \quad (6)$$

The rest of the circuit which consists of $Q_{17}$–$Q_{20}$ and $Q_{106}$–$Q_{107}$ is used as a level shifter which provides an output compatible to the CLK input of the AD7570.

The overall performance of the successive approximation A/D converter 70 depends on the speed and accuracy of the comparator 74. Because the DAC of the AD7570 has a current output, a low input impedance comparator is most suitable.

The DAC section of the AD7570 is a 10-bit multiplying DAC. The DAC circuit consists of ten single-pole, double-throw current steering switches and an "inverted" R-2R current weighting network. The output (OUT1) of this DAC can be treated as a parallel combination of a current source, $I_O$, a resistor, $R_O$, and a capacitor, $C_O$. The current, $I_O$, varies from $=0.32$ mA to $-0.32$ mA (for $V_{REF} = -3.2$ V). The resistance of RO varies from 5 kilohms to 7.5 kilohms. The capacitance of $C_O$ varies from 40 pf to 120 pf.

At the first half cycle ($t_0 \leq t < t_1$) of a clock pulse when $$i_E(t_0 \leq t < t_1) = 0 \quad (7)$$

$Q_{25}$ and $Q_{26}$ of the comparator circuit 74 are completely cut off and provide no positive feedback. The output current from the AD7570 is in the range $-0.32$ mA to $+0.32$ mA ($V_{REF} = 3.2$ V). This current is converted into a differential voltage, $v_{OUT1}$, across the collectors of the transistors $Q_{33}$ and $Q_{34}$ where $$-144 \text{ mV} \leq v_{OUT1} \leq +144 \text{ mV} \quad (8)$$

During the second half of the clock cycle ($t \geq t_1$), a latch current, $i_E$, is applied where $$i_E(t \geq t_1) = 0.25 \text{ mA} \quad (9)$$

For the purpose of illustration, it is asumed that right before the latch current is applied, $v_{OUT1}$ is positive and the voltages at the base of $Q_{23}$ and $Q_{25}$ are higher than those of $Q_{24}$ and $Q_{26}$. At $t = t_1$ the initial collector current of $Q_{25}$ will be larger than that of $Q_{26}$. The cross coupling configuration of $Q_{25}$ and $Q_{26}$ provides a regenerative action which increases the collector current of $Q_{25}$ rapidly until it is equal to the latch current, $i_E(t \geq t_1)$. This cuts off $Q_{26}$ completely. This regeneration circuit increases $v_{OUT1}$ by 100 mV.

This voltage is used to drive a simple single stage level shifter. Even though a PNP current mirror is employed in this comparator, the large over driving voltage ($|v_0| > 100$ mV) can produce a less than one microsecond switching time.

Because of the large voltage ($>100$ mV) applied to the differential pair, $Q_{30}$ and $Q_{31}$, the transistors are simply used to steer the 0.25 mA biasing current from the collector of $Q_{29}$. This provides a full $\pm 0.25$ mA driving capability at the output of the comparator. Since the comparator output is used to drive a CMOS input (COMP input of the AD7570) which is essentially a capacitive load, the output impedance can still provide proper operation. The speed of the comparator is governed by the loading capacitance. Assuming that the total parasitic capacitance (the combination of the collector parasitic capacitance of both the PNP and NPN transistors, the bonding pads and the CMOS input capacitance) to be 10 pF, the 0.25 mA output driving current can produce a slew rate ($\Delta V/\Delta t$) of about 25 V/us. This slew rate is more than adequate.

Sensor Amplifier

Figure 3:
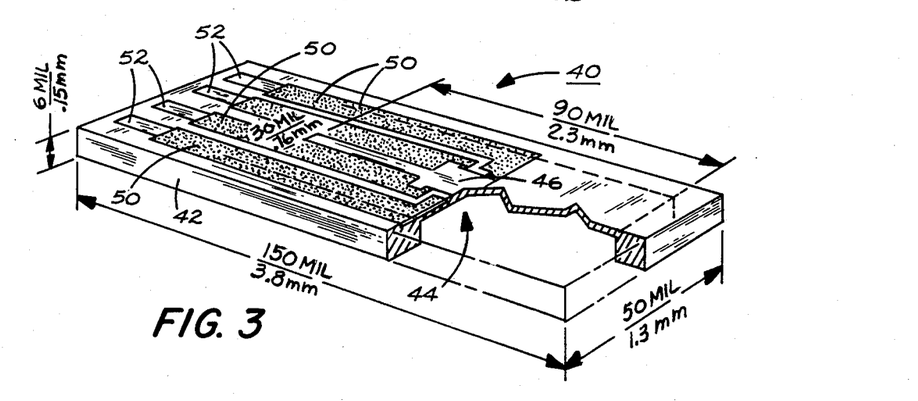
FIG. 3 is a perspective view of a pressure transducer or sensor forming a part of an implant.

The pressure sensor 40 has an output sensitivity of about 64 uV/mm Hg at 3.2 V excitation. For a dynamic pressure range of 250 mm Hg, the full scale output is only 16 mV. This signal must be amplified 150 to 250 times before it is applied to the A/D converter which has a full scale input of 3.2 V.

The signal bandwidth of the ICP signal is only dc-50 Hz. However, because the transducer is pulse powered and a steady state output is required within 20 usec after the application of power, the bandwidth requirement of the amplifier 72 is much higher.

The bandwidth requirement of the amplifier can be estimated assuming it has a true single pole response. The step response and the output error for the amplifier are given by the expressions $$E_{OUT} = a E_{IN}[1 - e^{-2\pi f_0 t}] \quad (10)$$

$$\epsilon = e^{-2\pi f_0 t} = \% \text{ error} \quad (11)$$

where
$E_{OUT}$ = the amplifier output voltage
$E_{IN}$ = the amplifier input voltage
a = the amplifier gain
$f_0$ = the amplifier signal bandwidth.

From the latter equation the required amplifier bandwidth for a given settling time and accuracy can be calculated. Assuming half of the settling time is required for the output to slew to the final voltage, then $t = 10$ us.

If the accuracy requirement is 0.1% or =0.001, from Eq. 11 we find $$2f_0 t \simeq 7 \quad (12)$$

and the minimum signal bandwidth, $f_0$, of the amplifier is found to be 100 KHz. This bandwidth, which is more than three orders of magnitude higher than the ICP signal bandwidth, increases the noise level. In order to minimize noise, a bipolar differential pair with collector resistor load input stage is used.

The amplifier must satisfy these two criteria:
(1) The amplifier is pulse powered. In the inactivated mode, it should dissipate no power.
(2) When not powered, the output of the amplifier must be maintained at ground potential so that no power is delivered to and dissipated by the internal thin film resistor network of the AD7570.

With reference to FIG. 10, the biasing currents of the amplifier are generated by the self-biased circuits consisting of $Q_{55}$ to $Q_{58}$, $Q_{63}$, $Q_{64}$, and $Q_{118}$ to $Q_{120}$. The current mirror configuration of $Q_{118}$ to $Q_{120}$ maintains equal currents at collectors of $Q_{56}$ and $Q_{57}$. $Q_{57}$ has twice the emitter area of $Q_{56}$ and, since the collector currents are the same, the voltage developed across $R_{50}$ is $$V_x = V_T \operatorname{Ln} 2 \quad (13)$$

and the collector currents $$I_{C56} = I_{C57} = \frac{V_T}{R_{50}} \ln 2 \quad (14)$$

where $V_T = kT/q$ is the thermal voltage approximately equal to 26 mV at room temperature. In this circuit, $R_{50} = 100$ ohms and $I_{C56}$ is found to be $$I_{C56} = 180 \text{ uA} \quad (15)$$

The collector current of $Q_{58}$ is simply three times that of $Q_{56}$ because of the triple emitter area, and $$I_{C58} = 540 \text{ uA} \quad (16)$$

The collector current of $Q_{63}$ can be calculated using an equivalent emitter resistor $$R_E = R_{57} + 2R_{59} \quad (17)$$

or $$R_E = R_{57} \quad (18)$$

if the node BIAS is shorted to ground. The equation which governs the collector current is $$I_{C63} R_E + V_T \ln \frac{I_{C63}}{I_S} = V_T \ln \frac{I_{C56}}{I_S} \quad (19)$$

Using Eq. 15, this equation is simplified to $$I_{C63} R_E = V_T \ln \frac{180 \text{ua}}{I_{C63}} \quad (20)$$

From Eqs. 17 and 18, $R_E$ is found to be either 28.8 kilohms or 14.4 kilohms. The solutions of Eq. 20 show a current of 3.5 uA or 6 uA.

Transistors $Q_{51}$ to $Q_{54}$ act as a start-up circuit for the selfbiased circuit to prevent it from entering and maintaining a zero current flow stable state. The start-up circuit, $Q_{51}$ to $Q_{54}$, insures that some current always flows in the transistors so that their current gain does not fall to a very low value. Once the circuit is operating, the emitter voltage of $Q_{54}$ is about 3 $V_{BE}$ and the start-up current is reduced to a negligible amount.

The input stage is a "simple differential pair" with a resistor load. Two emitter resistors, $R_{53}$ and $R_{54}$, are used to improve the linearity of this stage. Because of the small input signal range (less that 20 mV), this emitter degeneration function is sufficient to provide better that 0.1% FS linearity.

A second stage of the pressure transducer amplifier 72 includes of an operational amplifier with external feedback. The analysis of the operational amplifier follows closely with the analysis of a differential amplifier with "active load" given in the textbook by Gray entitled "Analysis and Design of analog Integrated Circuits", John Wiley & Sons Inc., New York, N.Y. (1977). Relevant portions of that text are incorporated herein by reference.

Figure 12:
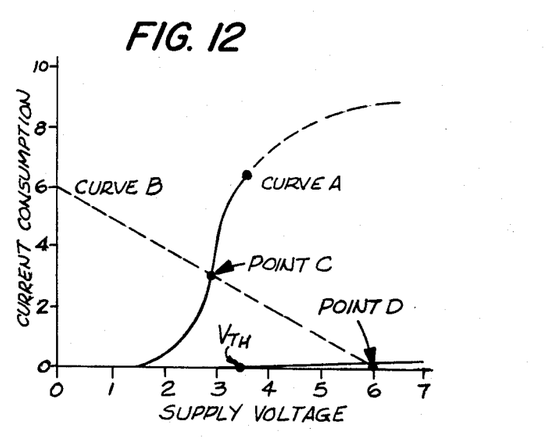
FIG. 12 is a graph showing telemeter current consumption as a function of supply voltage.

The current consumption as a function of the supply voltage of the complete telemeter 10 is shown in FIG. 12 as curve A. Before the supply voltage reaches $V_{TH}$ which is about 3.5 V, the telemeter's electronics are not in their proper operating condition and low duty cycle pulse powering has not taken effect. The current consumption reaches as high as 6 mA. Once the supply voltage is above $V_{TH}$, the low duty cycle pulse power circuit starts and the current consumption drops to about 50 uA. Consider the load line, B, which represents the output characteristics of the lithium battery with an output impedance of 1 KΩ. As shown in FIG. 12, when the telemeter is powered by this battery system, two stable operating points, C and D, are possible. Point D is the desirable operating point when the voltage is between 5 and 6 V and the current consumption is about 55 uA. However, if for any reason the supply voltage should fall below $V_{TH}$, the operating condition will be locked in at point C when the telemeter drains a large current (3 mA) and still is not operating properly. For this reason, a voltage monitor circuit consisting of transistors $Q_{42}$ to $Q_{48}$ and $Q_{114}$ to $Q_{117}$ is used (FIG. 10). The function of this circuit is to turn on the rest of the electronics if and only if, the supply voltage is above $V_{TH}$.

If the supply voltage is larger than $V_{TH}$ and the $\overline{\text{BUSY}}$ line from the AD7570 goes low, $Q_{114}$ and $Q_{116}$ will each initiate a current of about 650 uA. The collector current of $Q_{116}$ turns on $Q_{38}$ to $Q_{41}$ and generates a voltage equal to 2 $V_{BE}$ at node STROBE. This is the voltage which switches on all the current sources to activate the rest of the electronics. $Q_{40}$ and $Q_{41}$ mirror $Q_{116}$'s collector current which produces a negative voltage pulse across the $V_{BE}$ multiplier circuit ($Q_{37}$). This negative voltage pulse has an amplitude of (3.2 V + $V_{BE}$) which is used to generate a −3.2 V reference voltage.

The collector current of $Q_{114}$ produces a positive voltage pulse which is also (3.2 V + $V_{BE}$) in amplitude across a companion $V_{BE}$ multiplier circuit ($Q_{49}$). $Q_{50}$ is used as an emitter follower which produces a 3.2 V pulse to power the pressure transducer and the first stage of the pressure transducer amplifier.

Finally, transistors $Q_{21}$, $Q_{22}$ and $Q_{105}$ are used to generate the latch current for the latch comparator.

Command Receiver

Figure 13:
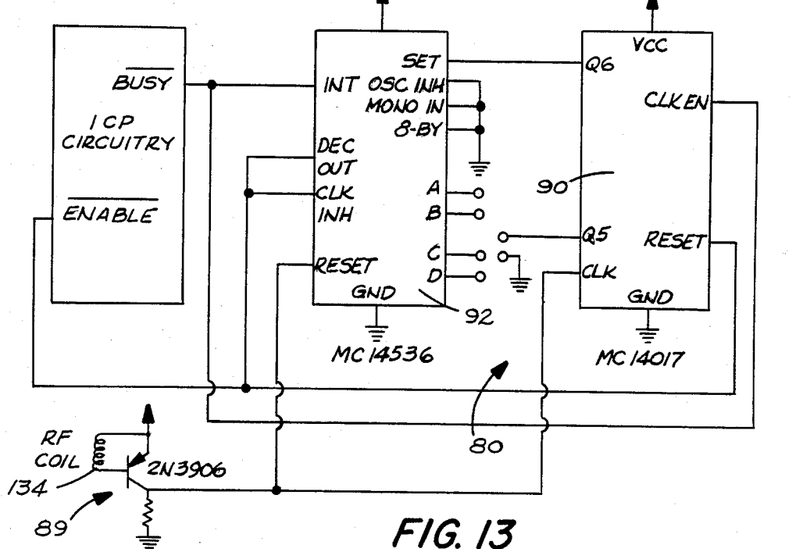
FIG. 13 is a schematic showing a command receiver for enabling the telemeter.

A RF command receiver 80 that controls the ON/-OFF state of the ICP telemeter is shown in FIG. 13. This command receiver is unique in that battery power is not directly switched, instead, the telemetry transmitter pulse generator stage is enabled/disabled. In this manner, the telemetry transmitter functions normally in enabled (ON) state, whereas in the disabled (OFF) state, data is not transmitted and only quiescent currents (less than one microampere for the entire implant) are drawn from the implanted batteries. An automatic power shutdown feature incorporated into the command receiver 80 disables the power drain (ON to OFF) after a specified ON period. This time interval is preset during construction to a value ranging from seconds up to approximately one day.

Commands are transmitted through a 3.5 MHz RF inductive link to the implanted command receiver. An input circuit 89 amplifies and rectifies the RF pulses of the proper frequency and relays a digital pulse of the same width to two CMOS logic circuits 90,92. These circuits performs a pulse width discrimination test upon the digital pulse. The CMOS logic also includes a programmable counter unit that performs an automatic shutdown function. The command receiver produces an $\overline{ENABLE}$ output which is connected to the thermistor, $R_{TH}$, of the pulse generator. This CMOS leveled output can swing from 0 V to $V_{CC}$. When $\overline{ENABLE}$ is LOW, the thermistor-controlled pulse generator functions as described above. When $\overline{ENABLE}$ is at $V_{CC}$, the pulse generator, along with all other electronics, are completely cut off resulting in a negligible quiescent supply current.

The input stage of this circuitry (a 2N3906 transistor, an RF coil and a 1 MΩ resistor) creates a digital pulse from an RF burst. The base emitter capacitance of the transistor and the Rf coil form a low Q tuned circuit which delivers a small base current to the transistor in the presence of the command signal carrier. This current is amplified and rectified by the transistor, thus delivering a collector current to the 1 MΩ resistor. This resistor, together with the input capacitance of the CMOS circuitry and the parasitic capacitance of the transistor itself, forms a low pass filter. Therefore, the high frequency components of the collector current are removed.

A digital pulse (on the order of milliseconds) is thus produced at the CMOS inputs. The amount of input power required to produce such a digital pulse is, at worst, about 0.1 microwatts and can easily be delivered by an external coil to the implant. In this design, sensitivity and selectivity are compromised. The low sensitivity, however, offers excellent noise and interference rejection, which automatically reduces the requirement of selectivity. The simplicity and reliability of this input stage offers definite advantages when compared to more sensitive and/or complex designs.

The two CMOS integrated circuits 90,92 provide the necessary logic for implementing the commands received and providing the automatic power shutdown feature. When a digital command pulse is relayed to the decade counter 90 from the input rectifier stage, its pulse width determines whether the decade counter recognizes the pulse as an ON, Off or invalid (noise) instruction. Pins A, B, C and D on the programmable counter 92 are set during construction to determine the ON interval which will occur before automatic power shutdown is triggered. Typically, time between $\overline{BUSY}$ clock pulses will be on the order of ten milliseconds. Based upon this estimate, ON intervals ranging from approximately 3 seconds to 24 hours can be chosen.

Overall System

The electronics of the telemeter 10 consists of a multichip hybrid circuit. Three commercially available CMOS IC's are used. (The AD7570 A/D converter for the pulse code modulation circuit and two CMOS MSI logic circuits 90,92 for the RF command switch). These are fairly dense IC's and no significant advantage can be gained by customization. Most of the bipolar circuits described above, however have very special functions and are not commercially available in an IC form. In order to minimize size, reduce component count and improve reliability, a custom bipolar IC is used in implementing these circuit functions. A few nonintegratable hybrid components (large value capacitors, coils, etc.) are also used.

Figures 14, 15:
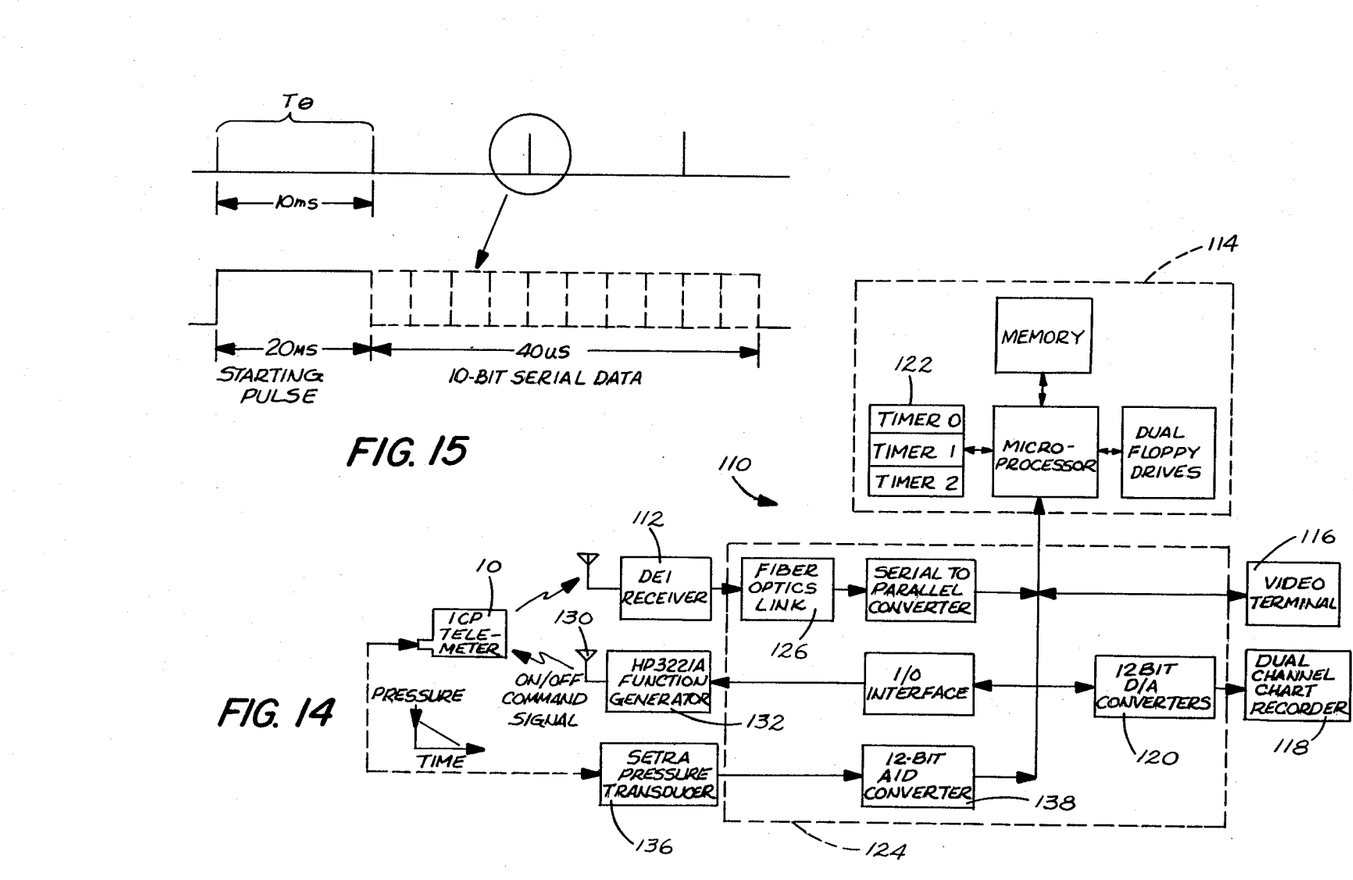
FIG. 14 is a schematic showing a system for monitoring outputs from the telemeter.
FIG. 15 is a timing diagram showing a sequence of data pulses from the telemeter.

A microcomputer based system 110 receives and demodulates output signals from the telemeter 10. The major equipment involved in the system 110 is shown in FIG. 14—A DEI receiver 112 manufactured by Defense Electronics, Division of DEI Industries, Rockville, Md. 20854 is used to recover the digital pulse signals. These pulse signals are then processed by a 8085 based microcomputer 114. A video terminal 116 is used as a display and an interface between the user and the system. A chart recorder 118 is interfaced to the microcomputer through two D/A converters 120 to provide hard copies of the temperature and pressure data.

The microcomputer 114 includes software programmable timers 122 used to measure the pulse period, $T_0$, (FIG. 15) of the telemetry signal. A first timer (Timer 0) is used to divide the microcomputer clock frequency from 2 MHz down to 10 KHz (period=100 μs). The second and the third timers (Timers 1 and 2) are connected in cascade and are clocked by the 10 KHz signal. In order to increase accuracy, $T_\theta$ is averaged over a period of about one second. As a result, $T_\theta$ (~10 ms) can be measured with an accuracy of about 0.01%.

A Telemetry Signal Interface 124 inclues a fiber optics link 126 and a serial-to-parallel converter 128. In order to minimize interference produced by the digital system, the RF receiver is isolated from the microcomputer through the use of the fiber optics link 126. The serial pulse signal at the fiber optics receiver is converted into a parallel format which is then processed by the microcomputer 114.

An ON/Off Command Transmitter 130 generates a pulsed RF signal for the telemeter's ON/OFF control 80. A HP3312A functional generator 132 is used to provide a 3.5 MHz RF signal. This signal is modulated by the microcomputer to produce a single RF burst which is either 55 ms (ON) or 10 ms (OFF) wide. This signal is coupled to the telemeter inductively through a circular coil.

A highly accurate Setra absolute pressure transducer 136 manufactured by Setra Systems, Inc., Twelve Huron Drive, Natick, Mass. 01760 is interfaced to the microcomputer 114 through a 12-bit A/D converter 138. This pressure transducer serves two functions. In demodulation, it measures the atmospheric pressure. By subtracting the atmospheric pressure from the telemetry signal, true differential intracranial pressure can be obtained. Secondly, in the characterization of the telemeter, this pressure transducer is used as a calibration reference.

The microcomputer compensates the pressure signal from the sensor 40 with atmospheric pressure and intracranial fluid temperature readings. A functional relationship is developed between temperature and pressure for each telemeter after it is assembled.

The temperature and intracranial pressure represented by $T_\theta(\sim 10$ ms) and X (0 to 1023) which is the numerical equivalent of the 10-bit serial data shown in FIG. 15. Since intracranial pressure is a linear function of the absolute input pressure, $P_{IN}$, to the telemeter, the following equation results:

$$X = X_{(P_{IN})} = a + b\, P_{IN} \tag{21}$$

In demodulating the telemetry signal, $P_{IN}$ is determined using the following equation, $$P_{IN} \cong P_{(X)} = A' + B'X \tag{22}$$

where $P_{(X)}$ is the demodulated pressure signal, A' and B' can be treated as the baseline and sensitivity of the pressure channel. Because of the nonzero temperature coefficients of the pressure transducer, both A' and B' are functions of temperature, $\theta_{IN}$. Equation (22) can be rewritten as $$P_{(X,\theta_{IN})} = A'_{(\theta_{IN})} + B'_{(\theta_{IN})} X \tag{23}$$

Since $T_\theta$ is a function of temperature, $\theta_{IN}$, Equation (23) may be rewritten using a transformation of variables as $$P_{(X,T_\theta)} = A_{(T_\theta)} + B_{(T_\theta)} X \tag{24}$$

where the baseline, $A_{(T_\theta)}$, and sensitivity, $B_{(T_\theta)}$, as a function of $T_\theta$ can be represented by the following polynomials:

$$A_{(T_\theta)} = \sum_{n=0}^{\infty} A_n T_\theta^n \tag{25}$$

$$B_{(T_\theta)} = \sum_{n=0}^{\infty} B_n T_\theta^n \tag{26}$$

Similarly, the demodulated temperature signal, $O_{(TO)}$, can be written as $$\theta_{IN} \cong \theta_{(T_\theta)} = \sum_{n=0}^{\infty} C_n T_\theta^n \tag{27}$$

$A_{(T_\theta)}$, $B_{(T_\theta)}$, and $\theta_{(T_\theta)}$ are well-behaved functions which can be adequately approximated by the first four terms of each of the polynomials. The resulting cubic equations are $$A_{(T_\theta)} = A_0 + A_1 \text{ is } T_\theta + 2 T_\theta^2 + A_3 T_\theta^3 \tag{28}$$

$$B_{(T_\theta)} = B_0 + B_1 T_\theta + B_2 T_\theta^2 + B_3 T_\theta^3 \tag{29}$$

$$\theta_{(T_\theta)} = C_0 + C_1 T_\theta + C_2 T_\theta^2 + C_3 T_\theta^3 \tag{30}$$

These three equations, along with equation (24) are used to demodulate the telemetry signals and carry out the necessary temperature compensation. In order to do this, the twelve constants, $A_0$ to $A_3$, $B_0$ to $B_3$ and $C_0$ to $C_3$, must be known. These constants vary from one telemeter to another and are obtained empirically.

Each telemeter is temperature cycled from 20° C. to 45° C. At a particular temperature, $\theta$, $T_\theta$ of the telemetry signal is measured. A negative ramp pressure signal is applied to the ICP telemeter in parallel to the Setra pressure transducer. This pressure signal is generated manually using a sphygmomanometer. A pressure of about 200 mm Hg is created by the inflating system. An exhaust valve is then adjusted to produce a slow pressure change (1 to 5 mm Hg/sec).

During this time, the pressure signal from the Setra transducer and the telemetry pressure signal (X) are acquired simultaneously by the microcomputer 114. The transfer characteristics $$P_{(X)} = A + BX \tag{31}$$

are obtained by a linear regression of 50 data points.

This process is repeated at fourteen different temperatures between 20° to 45° C. The three cubic equations are used to approximate these data. The constants ($A_0$ to $A_3$, $B_0$ to $B_3$ and $C_0$ to $C_3$) are obtained by a cubic regression on these data.

Generally, the temperature coefficients of the baseline are the sensitivity of the pressure transducer are fairly linear functions of temperature in the range of 20° to 45° C. However, a thermistor which has a non-linear temperature-resistance characteristic is used to measure the temperature. Consequently, the telemetered temperature signal, $T_\theta$, is a nonlinear function of the temperature. Since this variable is used to compensate for the temperature effects on the pressure channel, a polynomial instead of a linear equation must be used to approximate the nonlinear characteristics of the thermistor to provide accurate temperature compensation.

While the present invention has been described with a degree of particularity, certain alterations and/or modifications can be made in the disclosed system. It is the intent that the invention include all alterations and modifications falling within the spirit or scope of the appended claims.

We claim:

1. Apparatus for monitoring intracranial pressure in a subject, said apparatus comprising:
   a pressure transducer for monitoring pressure variations and producing an analog electronic signal output related to said pressure variations;
   means for coupling a fluid pressure from an intracranial cavity to said transducer;
   transmitter means having an analog to digital converter for converting said analog electronic signal output from said transducer into a sequence of digital data pulses to encode said pressure into a communication signal suitable for transmission to a remote receiver, said transmitter including switching means responsive to an external signal for switching said transmitter from a quiescent low power state to a higher power transmit state and circuitry coupled to said analog to digital converter for modulating the time between transmission of said sequence of digital data pulses in response to variations in temperature in a region of said pressure transducer; and
   means for hermetically encapsulating said transducer and said transmitter means having a through passage to accommodate said means for coupling.

2. The apparatus of claim 1 where the means for encapulating comprises a titanium package and the means for coupling comprises a titanium adapter connected to said titanium package for directing fluid to the vicinity of the pressure transducer.

3. The apparatus of claim 1 or 2 wherein said transducer comprises a piezoresistive diaphragm electrostatically bonded onto a glass tube having a passageway communicating with said means for coupling.

4. Apparatus for monitoring pressure changes in a subject comprising:
   a piezoresistive transducer mounted to said subject;
   a metal package for said transducer, said package including access means for routing a fluid whose pressure is to be measured inside said package to the vicinity of said transducer and further defining a pathway for allowing communicating signals inside said package;
   circuitry mounted inside said package, said circuitry including a low power analog to digital converter integrated circuit for converting electrical signals from said transducer into pulse code modulated communications signals for transmission to a remote receiver; and a second low power integrated circuit coupled to said analog to digital converter, said second integrated circuit having means for activating said circuitry in response to a signal external to said package from a quiescent low power state to a higher power transmitting state, amplifier means for amplifying an output from the transducer, and means for generating said pulse code modulated communications signals; and
   a battery within the metal package for powering said circuitry in both said quiescent and transmitting states.

5. The apparatus of claim 4 which additionally comprises means for montoring temperature variations in said fluid to enable corrections in pressure monitoring with temperature.

6. The apparatus of claim 4 or 5 which additionally comprises a remotely positioned receiver unit and means for storing signals representing said pressure variations.

7. Apparatus for monitoring pressure in a subject comprising:
   sensing means for monitoring pressure variations in a fluid, said sensing means including a piezoresistive pressure sensing diaphragm electrostatically bonded to a glass tube said tube having a center cavity in pressure communication with a region in said subject, said diaphragm partially bounding said cavity;
   circuitry mounted to the diaphragm for converting diaphragm response to pressure into an analog signal, and conversion circuitry for converting said analog signal into a digital communications signal suitable for transmission to a remote receiver;
   means responsive to the temperature in the vicinity of said sensing means to vary a frequency with which said digital communications signal is transmitted to said remote receiver thereby giving an indication of said temperature;
   a titanium package for hermetically encapsulating said transducer and said transmitter means within said subject, said package including a titanium adapter thermally sealed to said glass tube to couple fluid from the subject to the inside cavity of said glass tube.

8. The apparatus of claim 7 which additionally comprises means for receiving said digital signals, correlating the frequency of their receipt to the temperature in the vicinity of the sensing means and calculating a modified pressure based on the temperature and pressure of said fluid.

9. The apparatus of claim 7 wherein the means for encapsulating comprises a titanium package bounded by silicon rubber.

10. The apparatus of claim 9 wherein a battery is encapsulated in said titanium pack to power said means for converting.

11. The apparatus of claim 7 additionally comprising a switch for controlling operation of said means for converting by switching from a quiescent condition of low power consumption to an active condition of relatively greater power consumption.

12. Apparatus for monitoring a pressure level in a subject comprising:
   a pressure transducer mounted inside a hermetically sealed corrosion resistant package, said package including access means for coupling said transducer to a region inside said subject;
   circuitry mounted inside said package and coupled to said transducer for converting an analog pressure signal from said transducer into a digital pressure signal;
   transmitter means coupled to said circuitry for transmitting said digital signal from the subject to a remote receiving station;
   a battery mounted inside said package for powering said circuitry and said transmitter means;
   power control means mounted inside said package to switch said circuitry and transmitter means from a quiescent state where power drawn from said battery is relatively low to an active state during periods of data transmission where power drawn from said battery is relatively higher; and
   a temperature sensor mounted inside said package for measuring fluid temperature at the site of the pressure transducer; said temperature sensor coupled to said transmitter means which transmits both temperature and pressure data to said remote station.

13. The apparatus of claim 12 wherein said temperature sensor is part of pulse generator circuit coupled to said circuitry for converting analog pressure signals to digital pressure signals and where the sensor controls activation of this circuit by controlling a pulse repetition rate of said pulse generator circuit.

14. The apparatus of claim 12 where digital signal is pulse code modulated to reduce power consumption during data transmission.

15. The appatatus of claim 14 wherein a duty cycle of said pulse code modulation is related to the temperature of said sensor included in said power control means.

16. Apparatus for monitoring intracranial pressure in a subject comprising:
   a silicon substrate etched to form a piezoresistive diaphragm for monitoring pressure variations;
   a glass tube having a center cavity for routing a fluid from an intracranial cavity to a diaphragm surface; said tube electrostatically bonded to a non-etched region of said substrate;
   circuitry coupled to the diaphragm for converting movement of the diaphragm into a communication signal proportional to the pressure on the diaphragm suitable for transmission to a remote receiver; and
   a titanium package for encapsulating said diaphragm, glass tube and circuitry while isolating said glass tube from said circuitry, said package including a titanium adapter for routing fluid through said package to said center cavity, said package having an outer covering of silicon rubber to reduce discomfort to said subject.

17. The apparatus of claim 16 where the means for encapsulating further comprises a commercially pure titanium package and the means for routing comprises a titanium adapter connected to said titanium package for directing fluid to the vicinity of the pressure transducer.

18. Apparatus for monitoring intracranial fluid pressure in a subject comprising:
pressure sensing means for monitoring pressure variations in a fluid routed from an intracranial cavity to the pressure sensing means and producing an electronic output related to said pressure variations;
temperature sensing means for monitoring the temperature in the vicinity of said pressure sensing means;
means for transmitting a digital pressure communications signal corresponding to the pressure and for varying the frequency of transmission to give an indication of said temperature;
a remote receiver for receiving said digital communications signal; and;
programmable controller means for storing digital representations of said pressure and temperature and for monitoring atmospheric pressure at the vicinity of said programmable control means, said programmable controller means including demodulating means for calibrating the intracranial pressure reading with changes in temperature by monitoring changes in said digital pressure signal with calibration pressure and temperature conditions and calculating polynominal calibration co-efficiencies which define a relation between intracranial pressure, said pressure signal and the temperature indicated by said frequency.

19. The apparatus of claim 18 wherein said programmable controller means further comprises means for activating said means for transmitting.

* * * * *